US009757556B2

(12) United States Patent
O'Rourke et al.

(10) Patent No.: US 9,757,556 B2
(45) Date of Patent: Sep. 12, 2017

(54) LASER GENERATED SURFACE FINISHES FOR IMPLANTABLE MEDICAL DEVICES AND ELECTRODES

(71) Applicant: Cardiac Pacemakers, Inc., St. Paul, MN (US)

(72) Inventors: John O'Rourke, Clonmel (IE); Eoin P. Enright, Castleconnell (IE); Eric M. Petersen, Maple Grove, MN (US); Matthew P. Jones, Shoreview, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 0 days.

(21) Appl. No.: 14/966,945

(22) Filed: Dec. 11, 2015

(65) Prior Publication Data
US 2016/0166826 A1    Jun. 16, 2016

Related U.S. Application Data

(60) Provisional application No. 62/091,309, filed on Dec. 12, 2014.

(51) Int. Cl.
*A61N 1/05* (2006.01)
*A61N 1/39* (2006.01)
(52) U.S. Cl.
CPC ............ *A61N 1/05* (2013.01); *A61N 1/3956* (2013.01)
(58) Field of Classification Search
None
See application file for complete search history.

(56) References Cited

U.S. PATENT DOCUMENTS

| 4,434,189 | A | | 2/1984 | Zaplatynsky |
| 4,602,637 | A | | 7/1986 | Elmqvist et al. |
| 4,603,704 | A | * | 8/1986 | Mund ................ A61N 1/0565 607/116 |
| 5,290,368 | A | | 3/1994 | Gavigan et al. |
| 5,413,641 | A | | 5/1995 | Coulon |
| 5,587,200 | A | | 12/1996 | Lorenz et al. |
| 7,039,465 | B2 | | 5/2006 | Bardy et al. |
| 7,709,961 | B2 | | 5/2010 | Greenberg et al. |
| 2013/0282092 | A1 | | 10/2013 | Zhou et al. |

FOREIGN PATENT DOCUMENTS

| DE | 4324185 A1 * | 1/1995 | ............... A61N 1/05 |
| WO | WO0183837 A1 | 11/2001 | |

OTHER PUBLICATIONS

Yuan, Yuehua, et al. "Chapter 1: Contact Angle and Wetting Properties," In: Bracco, G., et al., Surface Science Techniques (Springer-Verlag Berlin Heidelberg, 2013), pp. 3-34.

* cited by examiner

*Primary Examiner* — Kennedy Schaetzle
(74) *Attorney, Agent, or Firm* — Faegre Baker Daniels LLP

(57) ABSTRACT

An electrode for use with an implantable medical device includes a titanium surface, and a titanium nitride layer formed on at least a portion of the titanium surface. At least some titanium of the portion of the titanium surface is removed from the titanium surface prior to forming the titanium nitride layer. The textured titanium nitride layer is formed by reacting nitrogen proximate to the portion of the titanium surface with titanium at the portion of the titanium surface.

12 Claims, 7 Drawing Sheets

LASER GENERATED SURFACE FINISHES FOR IMPLANTABLE MEDICAL DEVICES AND ELECTRODES

CROSS-REFERENCE TO RELATED APPLICATION

This application claims priority to Provisional Application No. 62/091,039, filed Dec. 12, 2014, which is herein incorporated by reference in its entirety.

TECHNICAL FIELD

The present invention relates to medical devices and methods for forming medical devices. More specifically, the invention relates to an electrode, an implantable device incorporating the electrode, and a method of processing the electrode.

BACKGROUND

Implantable medical devices, such as implantable cardioverter defibrillators, are used in a variety of therapeutic applications. In some implantable medical devices, a pulse generator and a medical lead, each having electrodes, are used together to provide electro stimulation therapy in the form of electrical pulses delivered to a tissue site within a patient. In some medical devices, the electrodes used to delivery therapy may also be used to sense conditions within the body that indicate the effectiveness of the therapy or indicate a need for additional therapy.

In some implantable medical devices, the delivery of therapy in the form of an electrical pulse may interfere with the ability of the device to subsequently sense the effectiveness of the therapy. In some implantable medical devices, such as an implantable cardioverter defibrillator, the electrical pulse may be delivered at a relatively high voltage, such as 1,000 volts (V), to provide effective therapy. In other devices, such as a subcutaneous implantable cardioverter defibrillator, the electrical pulse may be delivered at an even higher voltage, such as 3,000 V. The electrical pulse creates an electrical charge in and around the target tissue site. Once therapy is delivered, the electrical charge begins to dissipate. Until the charge dissipates, it may interfere with and prevent detection of conditions within the body that indicate the effectiveness of the therapy. At higher voltages, the electrical charge takes longer to dissipate. The delay between delivery of an electrical pulse and the time at which enough of the electrical charge has dissipated that the effectiveness of the therapy can be sensed is called the post-shock recovery time.

In some cases, a post-shock recovery time may be an important factor in the effective delivery of therapy. In cases where an initial electrical pulse does not result in a desired outcome and an additional electrical pulse may be required, a long post-shock recovery time will delay the additional therapy. In some cases, such a delay may reduce the overall effectiveness of the therapy. One way to dissipate the electrical charge more quickly, improve sensing capabilities, and reduce the post-shock recovery time is to decrease the impedance of at least one of the electrodes.

SUMMARY

In Example 1, a method of preparing an electrode for use with an implantable medical device, the electrode including a titanium surface, includes maintaining a nitrogen gas environment proximate to the titanium surface, delivering energy to a portion of the titanium surface, modifying the portion of the titanium surface with the energy delivered to the titanium surface, and forming titanium nitride by reacting titanium at the portion of the titanium surface with nitrogen from the nitrogen gas environment. Modifying includes increasing a surface area of the portion of the titanium surface, and removing titanium from the portion of the titanium surface. The titanium nitride is formed at the portion of the titanium surface where titanium has been removed.

In Example 2, the method of Example 1, wherein the titanium nitride formed at the portion of the titanium surface is a textured titanium nitride.

In Example 3, the method of any of Examples 1-2, wherein the energy is delivered to the portion of the titanium surface by a laser.

In Example 4, the method of Example 3, wherein removing titanium from the portion of the titanium surface includes evaporating by the laser.

In Example 5, the method of Example 3, wherein the laser is an ultrafast laser having a pulse width of between about 0.2 picoseconds and 15 picoseconds.

In Example 6, the method of Example 5, wherein removing titanium from the portion of the titanium surface includes stripping electrons from the portion of the titanium surface and producing a positively charged surface resulting in a Coulomb explosion that ejects titanium from the portion of the titanium surface.

In Example 7, the method of any of Examples 1-6, wherein maintaining a nitrogen gas environment proximate to the portion of the titanium surface includes directing a flow of nitrogen gas across the titanium surface and displacing other gases from the environment proximate to the portion of the titanium surface.

In Example 8, the method of any of Examples 1-6, wherein maintaining a nitrogen gas environment proximate to the portion of the titanium surface includes placing the electrode in a process chamber, pumping air out of the process chamber, and flowing nitrogen gas into the process chamber to maintain the nitrogen gas environment proximate to the portion of the titanium surface.

In Example 9, an electrode for use with an implantable medical device, preparable by the method of claim 1, includes a titanium surface, and a textured titanium nitride layer formed on at least a portion of the titanium surface.

In Example 10, the electrode of Example 9, wherein the textured titanium nitride layer includes a plurality of titanium nitride crystals characterized by an average crystal size, and the portion of the titanium surface has an average surface roughness, wherein the average surface roughness is greater than the average crystal size.

In Example 11, the electrode of Example 10, wherein the average surface roughness is at least ten times greater than the average crystal size.

In Example 12, the electrode of any of Examples 9-11, wherein the textured titanium nitride layer has a thickness between about 0.050 micrometers and 15 micrometers.

In Example 13, the electrode of any of Examples 9-12, wherein the implantable medical device includes an elongate lead, and the electrode is disposed proximate an end of the elongate lead.

In Example 14, the electrode of any of Examples 9-13, wherein the electrode is a metallic housing of an implantable medical device.

In Example 15, the electrode of any of Examples 9-14, wherein the implantable medical device is an implantable cardioverter defibrillator.

In Example 16, an electrode for use with an implantable medical device includes a titanium surface, and a textured titanium nitride layer formed on at least a portion of the titanium surface. At least some titanium of the portion of the titanium surface is removed from the titanium surface prior to forming the textured titanium nitride layer. The textured titanium nitride layer is formed by reacting nitrogen proximate to the portion of the titanium surface with titanium at the portion of the titanium surface.

In Example 17, the electrode of Example 16, wherein the textured titanium nitride layer includes a plurality of titanium nitride crystals characterized by an average crystal size, and the portion of the titanium surface has an average surface roughness, wherein the average surface roughness is greater than the average crystal size.

In Example 18, the electrode of Example 17, wherein the average surface roughness is at least 10 times greater than the average crystal size.

In Example 19, the electrode of any of Examples 16-18, wherein the textured titanium nitride layer has a thickness between about 0.050 micrometers and 15 micrometers.

In Example 20, the electrode of any of Examples 16-19, wherein the implantable medical device includes an elongate lead, and the electrode is disposed proximate an end of the elongate lead.

In Example 21, the electrode of any of Examples 16-19, wherein the electrode is a metallic housing of an implantable medical device.

In Example 22, a method of preparing an electrode for use with an implantable medical device, the electrode including a titanium surface, the method including: maintaining a nitrogen gas environment proximate to the titanium surface, delivering energy to a portion of the titanium surface, modifying the portion of the titanium surface with the energy delivered to the titanium surface, and forming titanium nitride by reacting titanium at the portion of the titanium surface with nitrogen from the nitrogen gas environment. Modifying includes increasing a surface area of the portion of the titanium surface, and removing titanium from the portion of the titanium surface. The titanium nitride is formed at the portion of the titanium surface where titanium has been removed.

In Example 23, the method of Example 22, wherein the titanium nitride formed at the portion of the titanium surface is a textured titanium nitride.

In Example 24, the method of any of Examples 22-23, wherein the energy is delivered to the portion of the titanium surface by a laser In Example 25, the method of Example 24, wherein removing titanium from the portion of the titanium surface includes evaporating by the laser.

In Example 26, the method of Example 24, wherein the laser is an ultrafast laser having a pulse width of between about 0.2 picoseconds and 15 picoseconds.

In Example 27, the method of Example 26, wherein removing titanium from the portion of the titanium surface includes stripping electrons from the portion of the titanium surface and producing a positively charged surface resulting in a Coulomb explosion that ejects titanium from the portion of the titanium surface.

In Example 28, the method of any of Examples 22-27, wherein maintaining a nitrogen gas environment proximate to the portion of the titanium surface includes directing a flow of nitrogen gas across the titanium surface and displacing other gases from the environment proximate to the portion of the titanium surface.

In Example 29, the method of any of Examples 22-27, wherein maintaining a nitrogen gas environment proximate to the portion of the titanium surface includes placing the electrode in a process chamber, pumping air out of the process chamber, and flowing nitrogen gas into the process chamber to maintain the nitrogen gas environment proximate to the portion of the titanium surface.

In Example, 30, an implantable medical device includes operational circuitry for providing electro stimulation therapy, and a metallic housing containing the operational circuitry. The housing includes a first external titanium surface, and a first external textured titanium nitride layer formed on at least a portion of the first external titanium surface to form a first electrode. The first electrode is electrically connected to the operational circuitry. At least some titanium of the portion of the first external titanium surface is removed from the first external titanium surface prior to forming the first external textured titanium nitride layer. The first external textured titanium nitride layer is formed by reacting nitrogen proximate to the portion of the first external titanium surface with titanium at the portion of the first external titanium surface.

In Example 31, the device of Example 30, further including an elongate lead, the lead including: a proximal end connected to the metallic housing, a distal end opposite the proximal end, and a second electrode disposed proximate to the distal end and electrically connected to the operational circuitry. The second electrode including: a second external titanium surface and a second external textured titanium nitride layer formed on at least a portion of the second external titanium surface. At least some titanium of the portion of the second external titanium surface is removed from the second external titanium surface prior to forming the second external textured titanium nitride layer. The second external textured titanium nitride layer is formed by reacting nitrogen proximate to the portion of the second external titanium surface with titanium at the portion of the second external titanium surface.

In Example 32, the device of any of Examples 30-31, wherein the implantable medical device is an implantable cardioverter defibrillator.

In Example 33, the device of any of Examples 30-32, wherein the first external textured titanium nitride layer includes a plurality of titanium nitride crystals characterized by an average crystal size, and the portion of the first external titanium surface has an average surface roughness, wherein the average surface roughness is greater than the average crystal size.

In Example 34, the device of any of Examples 30-33, wherein the average surface roughness is at least ten times greater than the average crystal size.

In Example 35, the device of any of Examples 30-34, wherein the first external textured titanium nitride layer has a thickness between about 0.050 micrometers and 15 micrometers.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
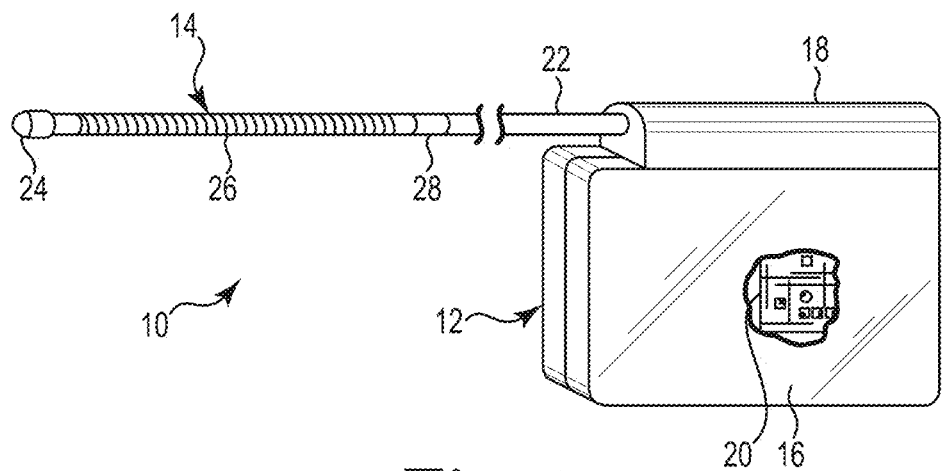
FIG. 1 is a schematic view of an implantable medical device including an electrode in accordance with embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
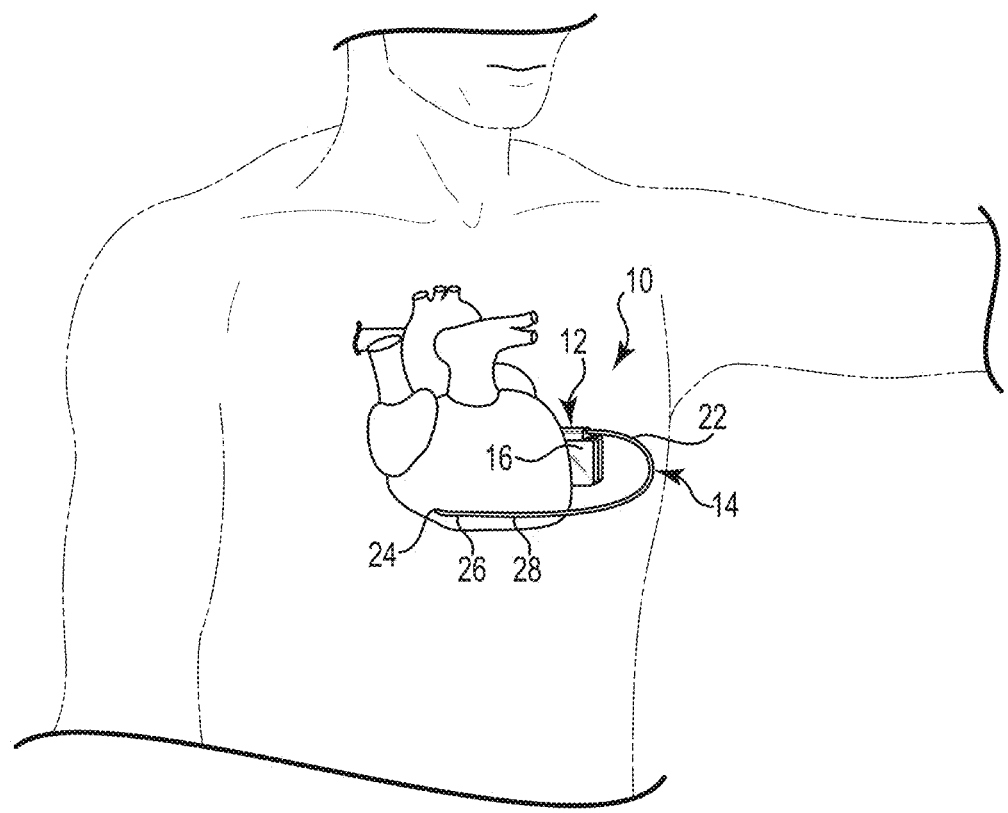
FIG. 2 is a schematic view of the implantable medical device of FIG. 1 subcutaneously implanted within a patient.

FIGS. 1 and 2 provide illustrative but non-limiting examples of medical applications using implantable medical devices having electrodes. In particular, FIG. 2 demonstrates a particular anatomical location within a patient's body where an implantable medical device having an electrode may be used. The application and location are illustrative only, as implantable medical devices having electrodes and incorporating embodiments of the present invention may be used in a variety of additional anatomical locations and for a variety of additional purposes.

FIG. 1 is a schematic view of an implantable medical device (IMD) 10. The IMD 10 includes a housing 12 and a lead 14. As shown, the housing 12 may include a housing electrode 16, a lead connector block 18, and operational circuitry 20. The lead 14 may include a proximal end 22, a distal end 24, a shock electrode 26, and a sensing electrode 28. In the embodiment of FIG. 1, the shock electrode 26 and the sensing electrode 28 are both located proximate to the distal end 24. Operational circuitry 20 may be contained within the housing 12 and may be configured to provide electro stimulation therapy in the form of electrical pulses. Operational circuitry 20 may also be used to sense conditions within the body that indicate the effectiveness of the therapy and/or indicate a need for additional therapy. The lead connector block 18 may connect the lead 14 to the housing 12 and to the operational circuitry 20 within. In the embodiment of FIG. 1, the housing 12 may be made of a biocompatible conductor, such as titanium, and an outer surface of the housing 12 may act as the housing electrode 16. In such a case, the lead connector block 18 may also isolate the lead 14 from housing electrode 16. In other embodiments, the housing 12 may be made of an isolating material and the housing electrode 16 may be a metal surface on the exterior of the housing 12. In either case, the housing electrode 16 may be electrically connected to the operational circuitry 20.

Lead 14 may be made of insulating material along most of its structure, for example, polyurethane or silicone. The insulating structure separates and isolates one or more electrodes, such as the shock electrode 26 and the sensing electrode 28, from each other. In the illustrated embodiment, the shock electrode 26 is illustrated as a coil electrode and the sensing electrode 28 is illustrated as a plate-type electrode extending circumferentially about the lead 14. However, it is understood that other electrode shapes, including flat plates and non-circumferentially extending electrodes, may be used. The shock electrode 26 and the sense electrode 28 may also be made of a biocompatible conductor, such as titanium. The shock electrode 26 and the sense electrode 28 may be electrically connected to the operational circuitry 20 by way of an electrical conductor (not shown) running within the lead 14 to the lead connector block 18.

FIG. 2 is a schematic view of the implantable medical device 10 of FIG. 1 subcutaneously implanted within a patient. As illustrated, in FIG. 2, the IMD 10 with the housing electrode 16 may be located in the left posterior axillary line approximately lateral to the tip of the inferior portion of the scapula. The lead 14 may traverse a subcutaneous path around the thorax, terminating with the distal end 24 disposed such that the shock electrode 26 and the sense electrode 28 are at the anterior precordial region. The distal end 24 may include additional features, such as an anchor device (not shown) to anchor the distal end 24 into tissue to hold the lead 14 in position following implantation.

Considering FIGS. 1 and 2 together, once implanted, the operational circuitry 20 may monitor voltages sensed between the housing electrode 16 on one side of the heart and the sense electrode 28 on the other side of the heart to determine whether or not the heart is beating with a normal heart rhythm. If tachycardia or fibrillation is detected, the operational circuitry 20 may generate an electrical pulse between housing electrode 16 on one side of the heart and the shock electrode 26 on the other side of the heart to deliver desired cardioversion/defibrillation therapy across the heart in an attempt to restore the heart to a normal rhythm. While the embodiment is discussed in terms of applying an electrical pulse, the electrical pulse is understood to represent a variety of electrical waveforms used for such therapy, including at least monophasic, biphasic, and multiphasic.

Following the cardioversion/defibrillation therapy, the operational circuitry 20 may again monitor voltages sensed between the housing electrode 16 on one side of the heart and the sense electrode 28 on the other side of the heart to determine whether or not a normal heart rhythm has been restored. If a normal rhythm is not restored, the process may repeat, with the operational circuitry 20 generating another electrical pulse between the housing electrode 16 on one side of the heart and the shock electrode 26, followed by monitoring voltages sensed between the housing electrode 16 on one side of the heart and the sense electrode 28 on the other side of the heart. However, during the post-shock recovery time between the electrical pulse of the cardioversion/defibrillation therapy and before the operational circuitry 20 can determine whether or not a normal heart rhythm has been restored, the operational circuitry 20 must wait until the voltage produced as part of the electrical pulse dissipates so that it does not interfere with detecting voltages associated with the rhythm of the heart. Until this post-shock recovery time has elapsed, the operational circuitry 20 may lack the information necessary to determine if additional cardioversion/defibrillation therapy is needed.

In some cases, the post-shock recovery delay may be long enough to reduce the overall effectiveness of the therapy. One way to dissipate the electrical charge more quickly and reduce the post-shock recovery time is to modify the surface structure and composition of one or more of the housing electrode 16 and the sense electrode 28 to reduce the electrical impedance of at least one of the electrodes. Modifying the surface composition to reduce the electrical impedance of the electrode increases the ability of the electrode to transfer current, thus dissipating the accumulated charge more quickly. Preparing an electrode to reduce its electrical impedance may be done by physically modifying the electrode surface to increase its surface area, and then forming a conductive layer at the modified electrode surface. The conductive layer formed at the modified electrode surface may be a textured layer. Within the meaning of this application, a textured layer is to be understood as a layer having elevations/protrusions and depressions in perpendicular direction to the plane or approximated plane of the layer surface. Such elevations/protrusions and depressions may include numerous physical features (bumps, crevasses, passageways, etc.) at a scale sufficient to present a much larger contact surface area to a conductive liquid, in comparison to an otherwise relatively smooth, non-textured electrode surface. Increasing the electrode surface area by physically modifying the electrode surface area and forming a conductive textured layer at the electrode surface to further increase the electrode surface area may increase the surface energy of the resulting electrode surface. Increasing the surface energy of the electrode surface allows for increased surface area contact to the conductive liquid.

Although FIGS. 1-2 illustrate an exemplary IMD in the form of a subcutaneously-implanted implantable cardioverter-defibrillator housing and lead system, the various embodiments can be implemented in any implantable medical device utilizing an implanted electrode for sensing intrinsic physiological electrical activity or delivering a therapeutic stimulus to patient tissue. Other such implantable medical devices include, without limitation, housings for pacemaker or cardiac resynchronization therapy devices, leadless pacing devices, endocardial leads, epicardial leads, neurostimulation systems such as spinal cord stimulation or deep brain stimulation device housings and associated leads, to name a few.

Figure 3:
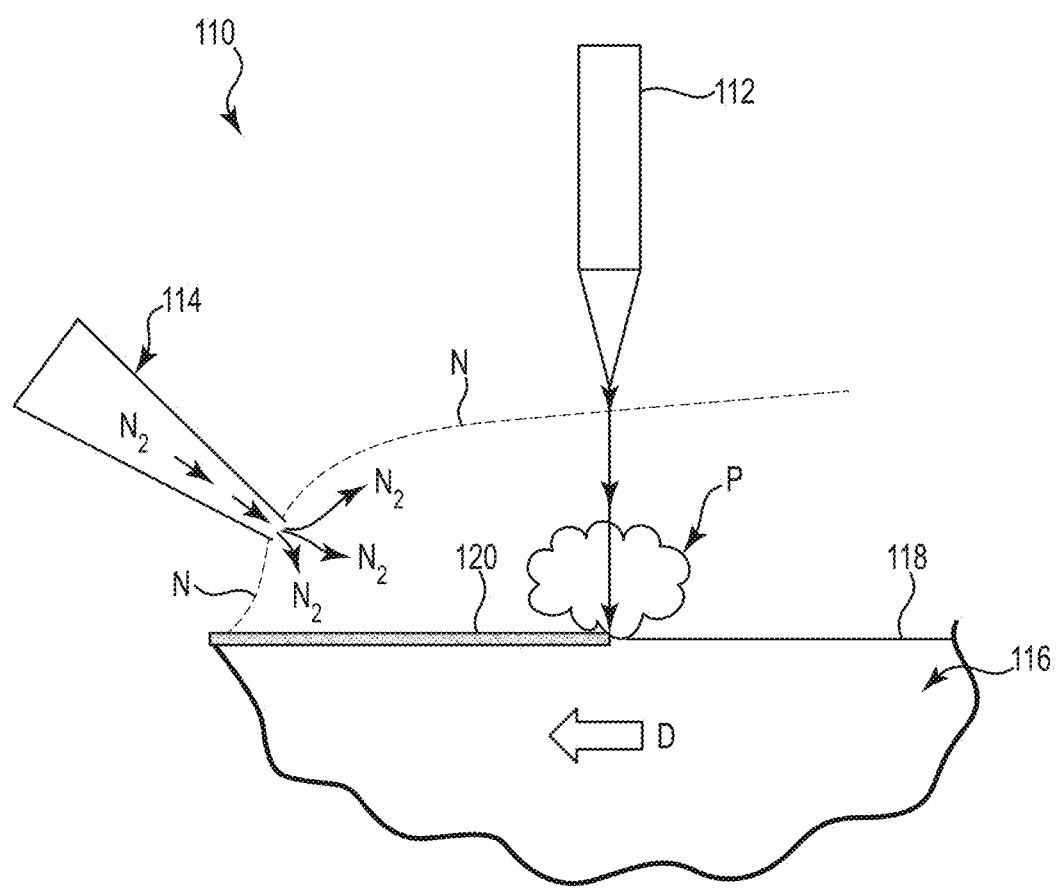
FIG. 3 is a schematic view illustrating a system for preparing an electrode for use with an implantable medical device in accordance with embodiments of the present invention.

FIG. 3 is a schematic cross-sectional view illustrating a system for preparing an electrode for use with an implantable medical device, such as the IMD 10 of FIGS. 1 and 2, in accordance with embodiments of the present invention. FIG. 3 shows a laser surface preparation system 110 including a laser 112 and a nitrogen distributor 114. FIG. 3 also shows a portion of an electrode 116. The electrode 116 may be, for example, the housing electrode 16, the shock electrode 26, or the sense electrode 28 of the IMD 10. Electrode 116 may include a titanium surface 118 and a titanium nitride layer 120. The electrode 116 may initially be formed entirely of titanium, or may be formed of a titanium sheet attached to an underlying base (not shown).

The nitrogen distributor 114 is configured to provide a flow of nitrogen gas, $N_2$, across a portion of the electrode 114, creating a nitrogen gas environment N. Nitrogen gas environment N is an environment proximate to the titanium surface 118 in which air may be pushed out and replaced by nitrogen gas, thus creating a nitrogen gas environment proximate to the titanium surface 118. Nitrogen distributor 114 may be, for example, a nozzle, series of nozzles, a manifold including a series of openings, or a combination of any of these.

The laser 112 may be configured to provide a pulse of energy to a portion of the titanium surface 118 within nitrogen gas environment N. Laser 112 may be, for example, a Q-switched neodymium-doped, yttrium aluminum garnet laser capable of delivering high peak energy pulses having a pulse width of, for example 150 nanoseconds. Alternatively, the laser 112 may be an ultrafast laser configured to deliver high peak energy pulses in less than, for example 15 picoseconds in some cases, or even less than 10 picoseconds.

In operation, the electrode 116 moves in direction D relative to the laser 112 (or alternatively, the laser 112 can move in a direction opposite of D relative to the electrode 116) as the laser 112 delivers pulses of energy to a portion of the titanium surface 118. As each pulse of energy from the laser 112 interacts with the titanium surface 118, titanium may be ablated, melted, and moved or splashed about, physically modifying the structure of portion of the titanium surface 118 and increasing its surface area. At the same time, titanium (mostly in the form of titanium oxide), may be removed, or ablated, from the portion of the titanium surface 118, forming a process region P within nitrogen gas environment N. Removal of the titanium freshly exposes titanium on the portion of the titanium surface 118 that may be in a high-energy condition due to the thermal energy remaining from the pulse of energy. In addition, some of the titanium removed from the portion of the titanium surface 118 may fall back onto the portion of the titanium surface 118 in a high-energy condition, and further physically modify the structure of the portion of the titanium surface 118 and further increase its surface area.

The titanium at the portion of the titanium surface 118 in a high-energy condition may react with the nitrogen gas from nitrogen gas environment N and form the titanium nitride layer 120. Thus, as the electrode 116 moves in direction D (or the laser 112 moves in a direction opposite of D), the titanium nitride layer 120 forms at the portion of the titanium surface 118.

The nature of the interaction between the laser 112 and the titanium surface 118 that removes titanium from the titanium surface 118 and forms the titanium nitride layer 120 may vary depending on the wavelength, pulse width and energy provided by the laser 112. By varying the nature of the interaction between the laser 112 and the titanium surface 118, the structure and surface area provided by the titanium nitride layer 120 may be tailored to specific electrode requirements. For example, the titanium nitride layer 120 may be a textured titanium nitride layer. In some embodiments, the textured titanium nitride layer 120 may be formed to a thickness of between 0.050 micrometers and 15 micrometers. In general the more thermal energy provided by the laser pulse, the greater the thickness of the textured titanium nitride layer 120 may be. In other embodiments, the textured titanium nitride layer 120 may be between 0.050 micrometers and 0.1 micrometers, or between 0.1 micrometers and 1 micrometer, or between 1 micrometer and 15 micrometers.

In some embodiments, when the pulse width may be relatively long, the temperature of the titanium surface 118 will rapidly increase, causing evaporation of titanium from the titanium surface 118 and into process region P. The fresh titanium surface following the evaporation of the titanium and the residual energy left from the laser pulse provide the high-energy conditions necessary for the titanium on the surface to react with the nitrogen gas to form titanium nitride. In some embodiments, the pulse width may be between about 15 picoseconds and about 1 millisecond. In other embodiments, the pulse width may be between 15 picoseconds and 1000 picoseconds, or between 1 nanosecond and 100 nanoseconds, or between 0.1 microseconds and 10 microseconds, or between 0.01 milliseconds and 1 millisecond. In some embodiments, energy delivered during the pulse may be between about 0.01 joules and 1 joule. In other embodiments, the energy delivered may be between 0.01 joules and 0.1 joules, or between 0.1 joules and 1 joule.

In other embodiments, when the laser pulse width may be much shorter, some of the incident energy may be transferred to free electrons in the titanium surface 118, and are ejected from the titanium surface 118 before they have time to transfer their energy to the surrounding titanium metal lattice in the form of thermal energy. This leads to a net positive charge developing at the titanium surface 118 causing the titanium atoms to start to repel each other. As the charge builds, some of the positively charged titanium atoms (and oxygen atoms) are expelled from the titanium surface 118 in what may be known as a Coulomb explosion. The resulting cloud of positively charged titanium atoms forms a plasma. The energy required to strip an electron from the titanium atom and expel it to form the plasma provides the high-energy conditions necessary for the titanium to react with the nitrogen gas to form titanium nitride on the freshly exposed surface. In some embodiments, the laser pulse width may be between about 0.2 picoseconds and about 15 picoseconds. In other embodiments, the laser pulse width may be between 0.2 picoseconds and 1 picosecond, or between 1 picosecond and 15 picoseconds. In some embodiments, energy delivered during the pulse may be between less than about 1 millijoule. In other such embodiments, the energy delivered may be less than 0.9 millijoules, 0.8 millijoules, 0.7 millijoules, 0.6 millijoules, 0.5 millijoules, 0.4, millijoules, 0.3 millijoules, 0.2 millijoules, and 0.1 millijoules.

In some embodiments, the spot size of the laser pulse may be less than 100 micrometers. In other embodiments, the spot size may be less than 90 micrometers, 80 micrometers, 70 micrometers, 60 micrometers, 50 micrometers, 40 micrometers, 30 micrometers, 20 micrometers, or 10 micrometers.

It may be beneficial to reduce contaminants, such as oxygen or water, in the nitrogen gas environment N. Such contamination of the nitrogen gas environment N may result in formation of other compounds such as titanium oxide, rather than the desired titanium nitride, which increases variability in the titanium nitride layer 120. Nitrogen distributor 114 may cause such contaminants to be displaced and replace them with nitrogen gas. An alternative system for creating the nitrogen gas environment N is illustrated in FIG. 4.

Figure 4:
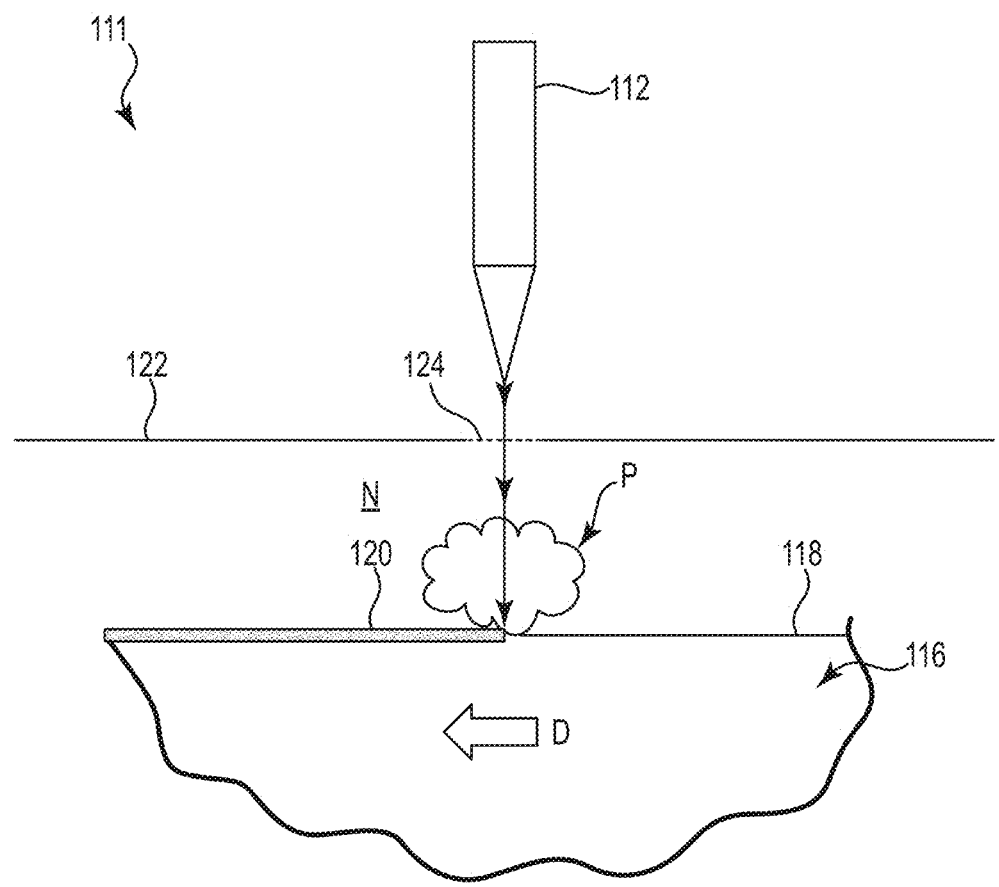
FIG. 4 is a schematic view illustrating an alternative system for preparing an electrode for use with an implantable medical device that can be used in relation to embodiments of the present invention.

FIG. 4 is a schematic cross-sectional view illustrating an alternative system for preparing an electrode for use with an implantable medical device, such as implantable medical device 10 of FIGS. 1 and 2, in accordance with embodiments of the present invention. FIG. 4 shows a laser surface preparation system 111. Laser surface preparation system 111 may be identical to the laser surface preparation system 110 described above in reference to FIG. 3, except that the nitrogen distributor 114 may be replaced by a process chamber 122. Process chamber 122 (only a portion shown) may include a window 124. The window 124 may be transparent to wavelengths used by the laser 112. The window 124 permits locating the laser 112 outside the process chamber 122.

The process chamber 122 may be a pressure vessel configured such that, once the electrode 116 is placed within, gases may be pumped out and nitrogen gas permitted to flow in to create the nitrogen gas environment N. In some embodiments, the process of pumping out gases and backfilling the process chamber 122 with nitrogen may be repeated to remove virtually all oxygen or water contamination from nitrogen gas environment N. Otherwise, operation of the laser surface preparation system 111 may be as for the laser surface preparation system 110 described above.

Figure 5:
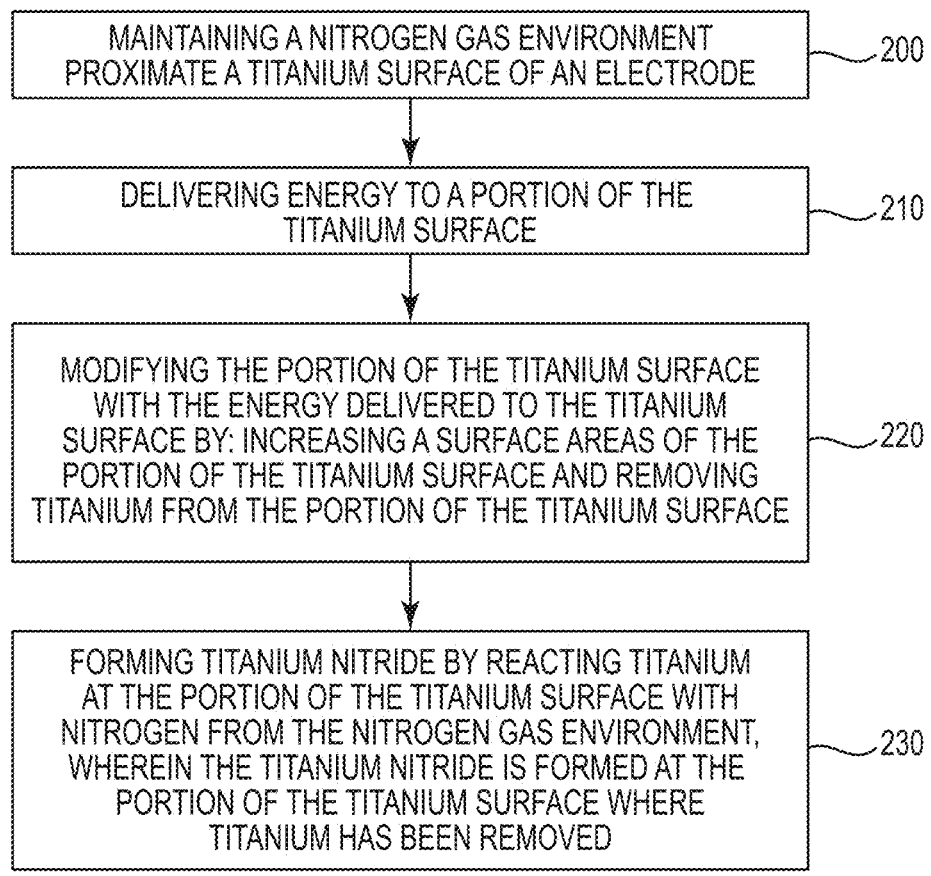
FIG. 5. is a flow diagram illustrating a method for preparing an electrode for use with an implantable medical device in accordance with embodiments of the present invention.

FIG. 5. is a flow diagram of an illustrative but non-limiting example of a method for preparing an electrode for use with an implantable medical device in accordance with embodiments of the present invention. A nitrogen gas environment may be maintained proximate to a titanium surface of the electrode, as generally indicated at block 200. Energy may be delivered to a portion of the titanium surface, as generally indicated a block 210. The portion of the titanium surface may be modified with the energy delivered to the titanium surface. The modification may be by increasing a surface area of the portion of the titanium surface, and by removing titanium from the portion of the titanium surface, as generally indicated at block 220. Titanium nitride may be formed by reacting titanium at the portion of the titanium surface with nitrogen gas from the nitrogen gas environment. The titanium nitride may be formed at the portion of the titanium surface where titanium has been removed, as generally indicated at block 230.

Figure 6:
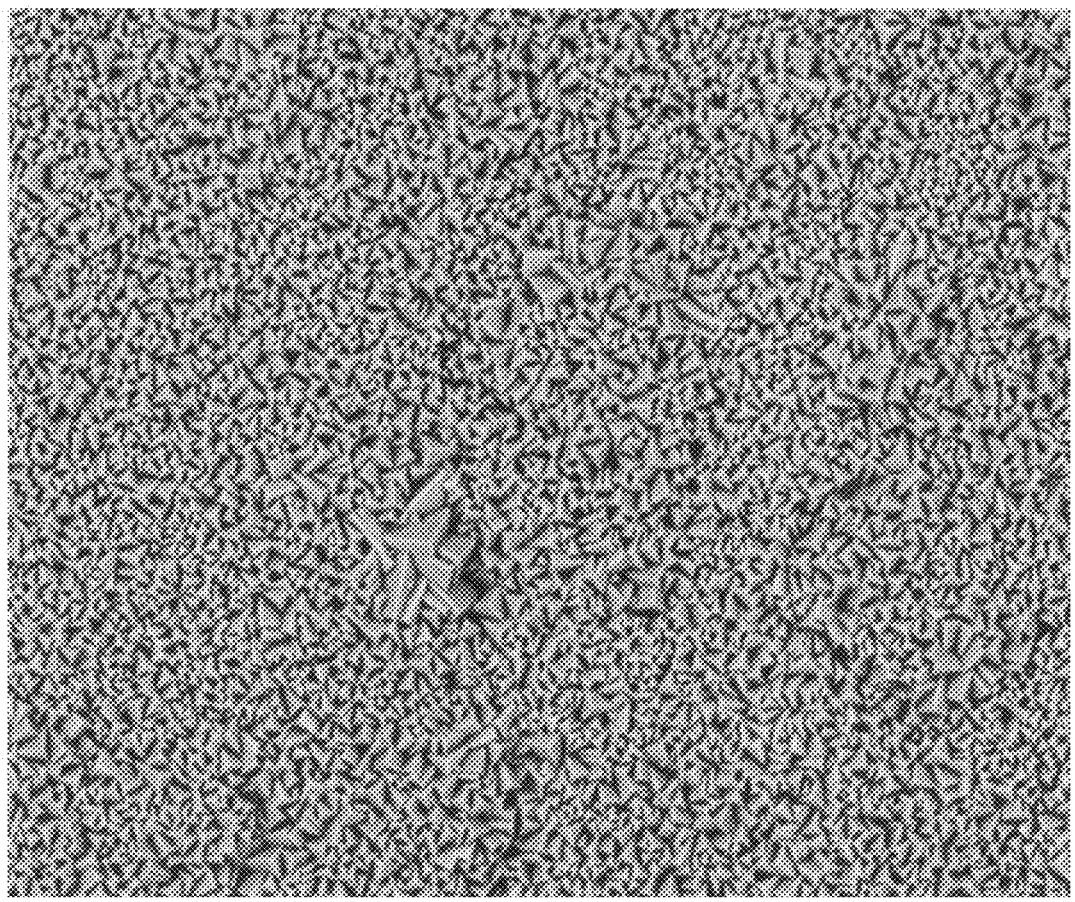
FIG. 6 is a scanning electron micrograph of a sputter deposited TiN surface as known in the art.
Figure 7:
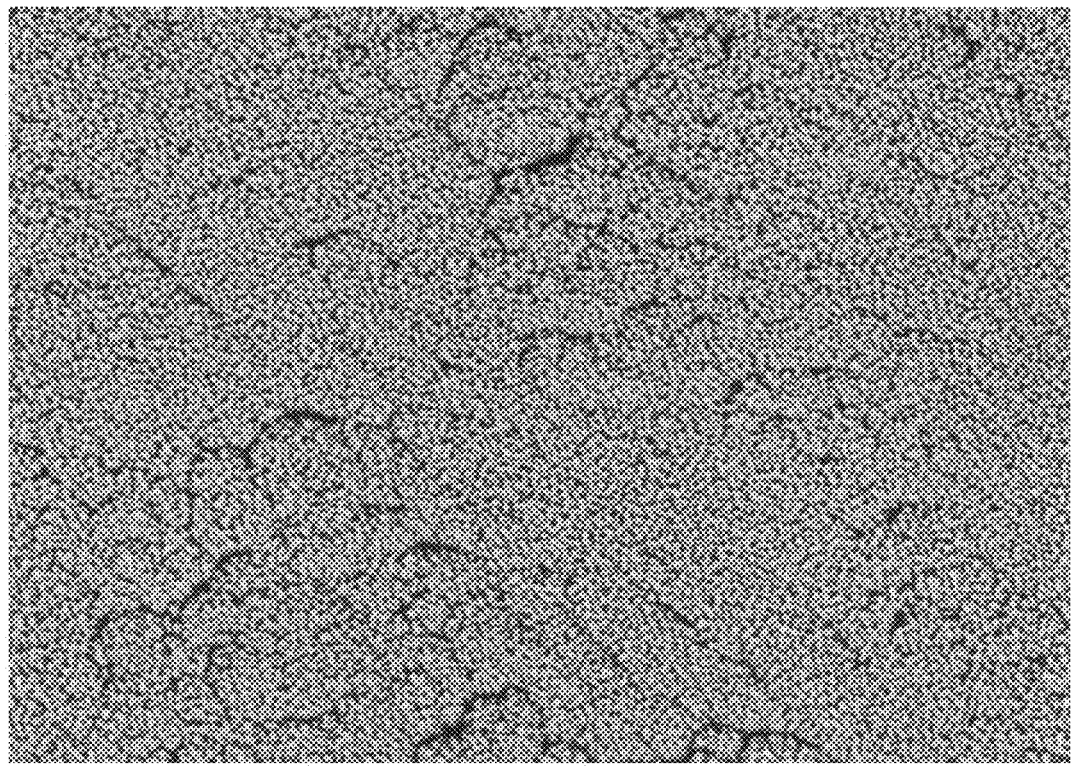
FIG. 7 is a scanning electron micrograph of another sputter deposited TiN surface as known in the art.
Figure 8:
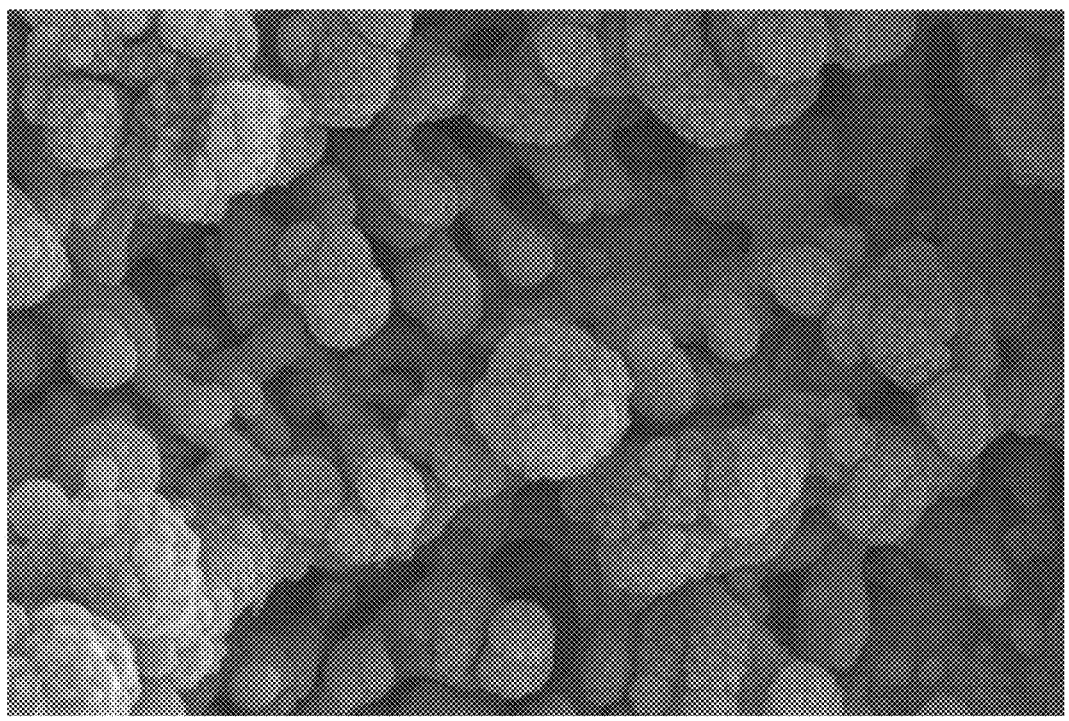
FIG. 8 is a scanning electron micrograph of a modified titanium surface with a TiN layer formed in accordance with embodiments of the present invention.

FIGS. 6, 7, and 8 together illustrate an increase in electrode surface area provided by an embodiment shown in FIG. 8 compared with processes known in the art.

FIG. 6 is a scanning electron micrograph of a sputter deposited titanium nitride surface as known in the art. The surface is magnified approximately 5,000 times. As evident from the FIG. 6, the average crystal size of the titanium nitride crystals is relatively large at about 1 micrometers. Larger crystals are preferred in applications where the titanium nitride layer may be deposited to protect an underlying surface, and not to provide an increase in surface area. Such layers are considered to be hard titanium nitride layers. As further apparent in FIG. 6, the titanium nitride crystals provide virtually all of the surface topography. The underlying surface upon which the titanium nitride layer is deposited appears to be relatively smooth, with an average surface roughness much less than the average titanium nitride crystal size.

FIG. 7 is a scanning electron micrograph of another sputter deposited titanium nitride surface as known in the art. The surface is magnified approximately 5,000 times. As evident from the FIG. 7, the average crystal size of the titanium nitride crystals is relatively small at about 0.1 micrometers, or at least ten times smaller than those observed for the hard titanium nitride layer in FIG. 6. Smaller crystals, or grains, of this size do form a textured titanium nitride layer because they are numerous features at a scale sufficient to present a much larger contact surface area to a conductive liquid, in comparison to an otherwise relatively smooth electrode surface. As further apparent in FIG. 7, the textured titanium nitride layer provides virtually all of the surface topography and increase in surface area. The underlying surface upon which the titanium nitride layer is deposited appears to be relatively smooth.

The titanium nitride coatings of FIGS. 6 and 7 are deposited by sputtering titanium from a titanium target using an argon/nitrogen plasma in a vacuum chamber. The sputtered titanium reacts with nitrogen in the argon/nitrogen plasma to form titanium nitride, which deposits onto all surfaces opposite the titanium target. Creating the plasma in the relatively large space between the titanium target and a surface upon which the titanium nitride is to be deposited requires the use of a vacuum chamber. Such systems may be costly and have long process cycle times due to the need to pump down, purge, and vent the vacuum chamber as part of the process. As a result, this may be a relatively expensive process. In addition, because the process deposits titanium nitride on all surfaces opposite the titanium target, separate masking operations are required to prevent deposition in certain areas, further increasing the expense.

FIG. 8 is a scanning electron micrograph of a titanium nitride surface in accordance with embodiments of the present invention. The surface is magnified approximately 5,000 times. As evident from the FIG. 8, the average crystal size of the titanium nitride crystals is relatively small at about 0.1 micrometers, forming a textured titanium nitride layer. However, as further apparent in FIG. 8, the textured titanium nitride layer is formed over a surface that is not smooth, but has an average surface roughness much greater than the average crystal size of the titanium nitride crystals. FIG. 8 shows some of the wide range of structures that may be formed when titanium is melted and moved or splashed about, physically modifying the structure of the titanium surface and increasing its surface area. The stalks, loops, and crevasses formed in accordance with embodiments described above and visible in FIG. 8 provide a significantly larger surface area upon which the textured titanium nitride layer may be deposited. The overall effect may be a dramatic increase in surface area resulting in a titanium nitride surface that has significantly lower impedance than prior art titanium nitride coatings.

Within the meaning of this application, average surface roughness is to be understood as an arithmetic average of the absolute values of vertical deviations of the profile from a mean line (Ra). Also, average crystal size is to be understood as an arithmetic average of crystal dimensions, the crystal dimensions being the visibly largest crystal dimension for each crystal.

As described above in reference to FIG. 3, depositing textured titanium nitride according to some embodiments may be done without the use of a vacuum chamber, resulting in considerable savings over processes requiring the use of a vacuum chamber. Also, because a laser can be programmed to scan only certain portions of the electrode surface, the textured titanium nitride layer may be controllably deposited on selected portions of the electrode surface without the need for an extra, costly masking operation. Finally, this ability to precisely control where on the electrode surface a textured titanium nitride surface may be deposited lends itself to creating optical patterns between coated and uncoated areas. In this way, optical patterns which may convey information, such as a trademark, model number, date, etc., may be produced at virtually no additional expense.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An electrode for use with an implantable medical device, the electrode comprising:
   a titanium surface; and
   a textured titanium nitride layer formed on at least a portion of the titanium surface, the textured titanium nitride layer having a thickness between 0.050 micrometers and 1 micrometer;
   wherein at least some titanium of the portion of the titanium surface is removed from the titanium surface prior to forming the textured titanium nitride layer wherein the textured titanium nitride layer is formed by reacting nitrogen proximate to the portion of the titanium surface with titanium at the portion of the titanium surface.

2. The electrode of claim 1 wherein the textured titanium nitride layer includes a plurality of titanium nitride crystals characterized by an average crystal size, and the portion of the titanium surface has an average surface roughness, wherein the average surface roughness is greater than the average crystal size.

3. The electrode of claim 2, wherein the average surface roughness is at least 10 times greater than the average crystal size.

4. The electrode of claim 1, wherein the textured titanium nitride layer has a thickness between about 0.050 micrometers and 0.10 micrometers.

5. The electrode of claim 1, wherein the implantable medical device includes an elongate lead, and the electrode is disposed proximate an end of the elongate lead.

6. The electrode of claim 1, wherein the electrode is a metallic housing of an implantable medical device.

7. An implantable medical device comprising:
   operational circuitry for providing electro stimulation therapy; and
   a metallic housing containing the operational circuitry, the housing including:
   a first external titanium surface; and
   a first external textured titanium nitride layer formed on at least a portion of the first external titanium surface to form a first electrode, the first electrode electrically connected to the operational circuitry, the first external textured titanium nitride layer having a thickness between 0.050 micrometers and 1 micrometer;
   wherein at least some titanium of the portion of the first external titanium surface is removed from the first external titanium surface prior to forming the first external textured titanium nitride layer, wherein the first external textured titanium nitride layer is formed by reacting nitrogen proximate to the portion of the first external titanium surface with titanium at the portion of the first external titanium surface.

8. The device of claim 7, further comprising an elongate lead, the lead including:
   a proximal end connected to the metallic housing;
   a distal end opposite the proximal end; and
   a second electrode disposed proximate to the distal end and electrically connected to the operational circuitry, the second electrode including:
   a second external titanium surface; and
   a second external textured titanium nitride layer formed on at least a portion of the second external titanium surface;
   wherein at least some titanium of the portion of the second external titanium surface is removed from the second external titanium surface prior to forming the second external textured titanium nitride layer, wherein the second external textured titanium nitride layer is formed by reacting nitrogen proximate to the portion of the second external titanium surface with titanium at the portion of the second external titanium surface.

9. The device of claim 8, wherein the implantable medical device is an implantable cardioverter defibrillator.

10. The device of claim 7, wherein the first external textured titanium nitride layer includes a plurality of titanium nitride crystals characterized by an average crystal size, and the portion of the first external titanium surface has an average surface roughness, wherein the average surface roughness is greater than the average crystal size.

11. The device of claim 10, wherein the average surface roughness is at least ten times greater than the average crystal size.

12. The device of claim 10, wherein the first external textured titanium nitride layer has a thickness between about 0.050 micrometers and 0.10 micrometers.

* * * * *